United States Patent [19]

Ruckes et al.

[11] Patent Number: 5,063,252
[45] Date of Patent: Nov. 5, 1991

[54] PROCESS FOR THE PRODUCTION OF PLASTICS BY THE POLYISOCYANATE POLYADDITION PROCESS AND CATALYSTS SUITABLE FOR THIS PROCESS

[75] Inventors: Andreas Ruckes, Leverkusen; Martin Brock, Cologne; Richard Weider, Leverkusen, all of Fed. Rep. of Germany

[73] Assignee: Bayer Aktiengesellschaft, Bayerwerk, Fed. Rep. of Germany

[21] Appl. No.: 433,315

[22] Filed: Nov. 7, 1989

[30] Foreign Application Priority Data

Nov. 10, 1988 [DE] Fed. Rep. of Germany ....... 3838128

[51] Int. Cl.$^5$ ..................... C08G 18/20; C07F 9/6584
[52] U.S. Cl. ........................................ 521/108; 564/13
[58] Field of Search ........................ 521/108; 528/76; 564/13

[56] References Cited

U.S. PATENT DOCUMENTS 4,595,445 6/1986 Hombach et al. ............... 156/307.3

FOREIGN PATENT DOCUMENTS 1182014 2/1970 United Kingdom .

OTHER PUBLICATIONS

Becker/Braun, Kunststoff-Handbuch, vol. VII, "Polyurethane", 1983, pp. 90–97 CHIMIA 39, 1985, p. 269.

Primary Examiner—John Kight, III
Assistant Examiner—Shelley A. Wright
Attorney, Agent, or Firm—Joseph C. Gil; Thomas W. Roy

[57] ABSTRACT

The present invention is directed to a process for the production of polyurethanes using catalysts based on triamino(imino)phosphoranes corresponding to formulas I, II or III

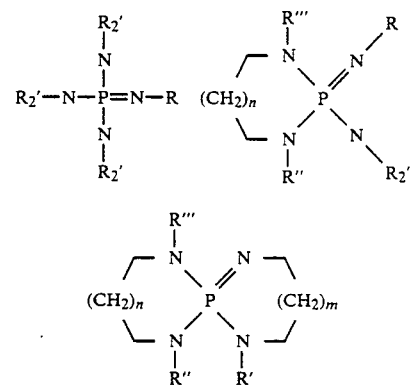

wherein
R, R', R'' and R''' represent hydrocarbon substituents and
n and m may be the same or different and represent 0, 1 or 2.

The present invention also relates to certain of the triamino(imino)phosphoranes used as catalysts.

1 Claim, No Drawings

PROCESS FOR THE PRODUCTION OF PLASTICS BY THE POLYISOCYANATE POLYADDITION PROCESS AND CATALYSTS SUITABLE FOR THIS PROCESS

BACKGROUND OF THE INVENTION

1. Field of the Invention

This invention relates to a process for the production of polyurethanes using substituted triamino(imino)phosphoranes as catalysts. These catalysts may be used as a substitute for, or in combination with, urethane catalysts known per se, for example for the production of rigid or flexible polyurethane foams and many other polyurethane products. In the context of the invention, polyurethane products are understood to be any reaction products of polyisocyanates of compounds containing at least two isocyanate-reactive hydrogen atoms, i.e., the term polyurethane as used in the present context is understood to encompass, for example, pure polyurethanes, polyurethane polyureas or pure polyureas.

2. Description of the Prior Art

The rate of reaction between isocyanate groups and compounds containing NCO-reactive hydrogen atoms is influenced not only by the temperature of the starting products and their structure, but more importantly by suitable catalysts. In practice, bases (for example tertiary amines such as triethyl amine) are predominantly used as nucleophilic catalysts while organometallic compounds (for example Sn carboxylates such as Sn(III) octoate) are predominantly used as electrophilic catalysts. The combined use of Lewis acids and Lewis bases, which is normally characterized by synergistic effects, is known. However, it is also known that, in many applications, amines are solely used as catalysts.

Of the large number of known amine catalysts (cf. Kunststoff-Handbuch, Vol. VII, Polyurethane, Hansen-Verlag, Munchen, 1983, pages 92–98), relatively few have previously been adopted for wide scale use in practice. Those which have include 1,4-diazabicyclo[2.2.2]-octane (DABCO), bis-(2-dimethylaminoethyl)-ether, triethyl amine, dimethyl cyclohexyl amine, dimethyl ethanolamine, dimethyl benzyl amine, methyl morpholine and ethyl morpholine to name the most important. Catalysts distinguished by high activity, economic production and broad spectrum application are of course used above all. Another aspect gaining in importance is the toxicological evaluation of the catalysts in regard to processing safety and odor emission. Many of the amine catalysts used today, including DABCO and triethyl amine, are unsatisfactory due to their high volatility and their relatively strong amine odor which is transmitted to the end product produced therefrom. In view of the many potential applications of polyurethane plastics, it is equally desirable to provide catalysts "custom-made" to suit particular requirements. One possibility is to chemically modify a given type of catalyst to adapt its activity to the particular application envisaged.

Another class of compounds suitable as basic polyurethane catalysts are the bicyclic amidines described in DE-OS 1,745,418 which are comparable in activity with the strongest of the previously known amine bases and which also have a considerably weaker odor. However, a serious disadvantage of these compounds which has previously restricted their application lies in their poor hydrolysis stability which, in view of the frequent use of water as a blowing agent or chain extender in polyurethane systems, largely precludes their use because the corresponding formulations are not stable in storage.

It has now surprisingly been found that certain triamino(imino)phosphoranes may be used with advantage as catalysts for the production of polyurethanes and also polyepoxide resins.

The compounds to be used in accordance with the invention show high stability to hydrolysis and, thus, are not sensitive to atmospheric moisture or water. In addition, they show even higher catalytic activity when compared to the bicyclic amidine bases mentioned above. Another welcome effect of the catalysts proposed in accordance with the invention is that, in contrast for example to DABCO which may not be chemically altered under economically reasonable conditions, the activity of the products can be "tailored" by the choice of suitable substituents at the nitrogen. Further advantages of the compounds are their weak odor and their low volatility which leads to a distinct reduction in odor emission during the production of polyurethane products.

Further advantages include ease of handling (because the triamino(imino)phosphoranes used are liquid), good hardening behavior and also the very simple production of some of the compounds.

SUMMARY OF THE INVENTION

The present invention is directed to a process for the production of polyurethanes using substituted triamino(imino)-phosphoranes corresponding to formulas I, II or III

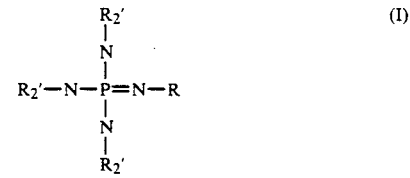

(I)

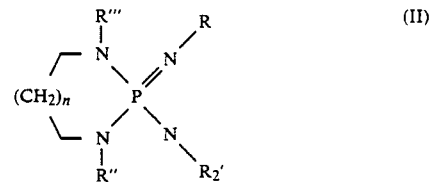

(II)

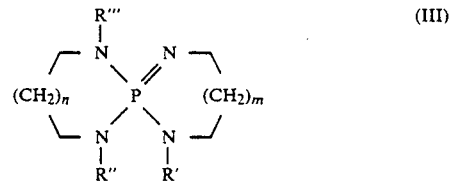

(III)

wherein

R represents hydrogen, linear or branched alkyl groups containing 1 to 8 carbon atoms, cycloalkyl or alkylcycloalkyl groups containing 5 to 9 carbon atoms, aryl groups or alkylaryl groups, R' represents linear or branched alkyl groups containing 1 to 8 carbon atoms, cycloalkyl or alkylcycloalkyl groups containing 5 to 9 carbon atoms, cycloalkylene groups containing 4 to 6 carbon atoms, R" represents hydrogen, linear or branched alkyl groups containing 1 to 8 carbon atoms, cycloalkyl or alkylcycloalkyl groups containing 5 to 9 carbon atoms, aryl groups or alkylaryl groups, R''' represents linear or branched alkyl groups containing 1 to 8 carbon atoms, cycloalkyl or alkylcycloalkyl groups containing 5 to 9 carbon atoms, aryl groups or alkylaryl groups and n and m may be the same or different and represent 0, 1 or 2, as catalysts.

The present invention also relates to compounds corresponding to general formula (II) wherein R represents hydrogen, linear or branched alkyl groups containing 1 to 8 carbon atoms, cycloalkyl or alkylcycloalkyl groups containing 5 to 9 carbon atoms, aryl or alkylaryl groups, R' represents linear or branched alkyl groups containing 1 to 8 carbon atoms, cycloalkyl or alkylcycloalkyl groups containing 5 to 9 carbon atoms or cycloalkylene groups containing 4 to 6 carbon atoms, R'' represents hydrogen, linear or branched alkyl groups containing 1 to 8 carbon atoms, cycloalkyl or alkylcycloalkyl groups containing 5 to 9 carbon atoms, aryl groups or alkylaryl groups, R''' represents linear or branched alkyl groups containing 2 to 8 carbon atoms, cycloalkyl or alkylcycloalkyl groups, aryl or alkylaryl groups and n is 0, 1 or 2;

compounds corresponding to general formula (II) wherein

R represents hydrogen, linear or branched alkyl groups containing 1 to 8 carbon atoms, cycloalkyl or alkylcycloalkyl groups containing 5 to 9 carbon atoms, aryl or alkylaryl groups, R' represents a methyl group or branched alkyl groups containing 3 to 8 carbon atoms, cycloalkyl or alkylcycloalkyl groups containing 5 to 9 carbon atoms or cycloalkylene groups containing 4 to 6 carbon atoms, R'' represents hydrogen, linear or branched alkyl groups containing 1 to 8 carbon atoms, cycloalkyl or alkylcycloalkyl groups containing 5 to 9 carbon atoms, aryl or alkylaryl groups, R''' represents linear or branched alkyl groups containing 1 to 8 carbon atoms, cycloalkyl or alkylcycloalkyl groups containing 5 to 9 carbon atoms, aryl or alkylaryl groups and n is 0, 1 or 2; and compounds corresponding to general formula (III) wherein R represents hydrogen, linear or branched alkyl groups containing 2 to 8 carbon atoms, cycloalkyl or alkyl cycloalkyl groups containing 5 to 9 carbon atoms, aryl or alkylaryl groups, R' represents linear or branched alkyl groups containing 1 to 8 carbon atoms, cycloalkyl or alkylcycloalkyl groups containing 5 to 9 carbon atoms or cycloalkylene groups containing 4 to 6 carbon atoms, R'' represents hydrogen, linear or branched alkyl groups containing 1 to 8 carbon atoms, cycloalkyl or alkylcycloalkyl groups containing 5 to 9 carbon atoms, aryl or alkylaryl groups, R''' represents hydrogen, linear or branched alkyl groups containing 1 to 8 carbon atoms, cycloalkyl or alkylcycloalkyl groups containing 5 to 9 carbon atoms, aryl or alkylaryl groups and n and m may be the same or different and represent 0, 1 or 2.

DETAILED DESCRIPTION OF THE INVENTION

Preferred catalysts are:

N,N',N''-hexamethyl-triamino(methylimino)phosphorane

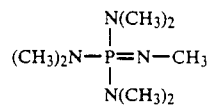

N,N',N''-hexaethyl-triamino(methylimino)phosphorane

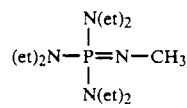

N,N',N''-hexamethyl-triamino(t-butylimino)phosphorane, 2-t-butylimino-2-diethylamino-1-methylperhydro-1,3,2-diazaphosphorine

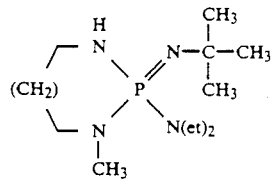

2-t-butylimino-2-diethylamino-1,3-dimethylperhydro-1,3,2-diazaphosphorine, 7-ethyl-5,11-dimethyl-1,5,7,11-tetraza-6-phosphaspiro-[5.5]undec-1(6)-ene

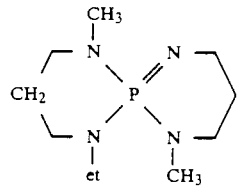

The triaminoiminophosphoranes corresponding to general formulae (I) to (III) are prepared by known reaction mechanisms.

Compounds corresponding to general formula (I) may be prepared, for example, by reaction of phosphorous acid triamides (prepared from phosphorus trichloride and secondary amines) with N-substituted chloroamines or alkylazides with elimination of hydrogen chloride and nitrogen in accordance with the following equation:

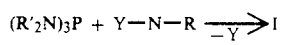

wherein Y represents HCl, $N_2$

[see K. Issleib, M, Lischewski, Synth. Inorg. Met. Org. Chem. 3 (1973) 255; P. Hassmann, 3. Goueau, Z. anorg. allg. Chem. 408 (1974) 293] or by treatment of triaminohalophosphonium halides prepared by halogenation of the phosphorous acid triamides mentioned above with primary amines or ammonia in accordance with the following equation:

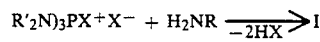

wherein x represents halogen (see G.N. Koidan et Ja., Zh. Obsh. knim. 52 (1982) 2001).

Compounds corresponding to general formula (II) may be prepared in a multistep synthesis (see R. Schwesinger, Chimia 39 (1985) 269) from N-substituted iminophosphorus trichlorides by treatment with a secondary amine and subsequent reaction with an N-monosubstituted-α,ω-diaminoalkane in accordance with the following equation:

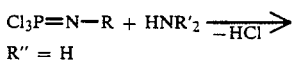

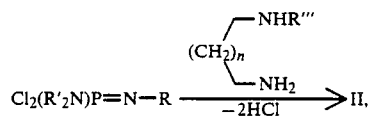

wherein R'' represents hydrogen.

The compounds thus obtained (R''=H) may optionally be converted by treatment with suitable alkylating agents into compounds corresponding to formula II wherein R'' represents H.

Compounds corresponding to general formula III may be obtained by a multistep synthesis also described by Schwesinger from phosphorus pentachloride and N-monosubstituted-α,ω-diaminoalkanes in accordance with the following equation

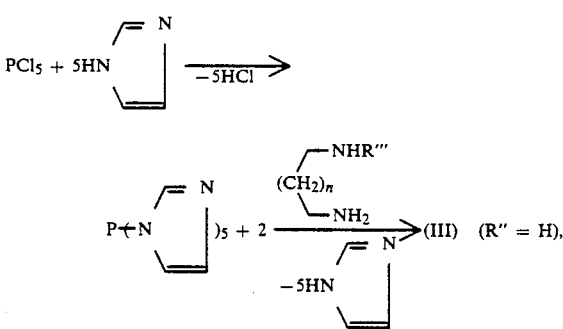

The resulting compounds corresponding to formula III (R''=H) may optionally be converted by treatment with suitable alkylating agents into compounds corresponding to formula III in which R''=H. To improve the yield of the monoalkylation, one of the two reactive nitrogen atoms may have to blocked by a suitable protective group. After alkylation of the second reactive nitrogen atom, the protective group is removed again by standard methods.

The described processes for the production of the triaminoiminophosphoranes corresponding to general formulas I to III enable a variety of previously unknown compounds to be synthesized.

It is possible to adapt the properties of the triaminoiminophosphoranes to the application envisaged through the choice of various amines and by modification of the substituent R''.

The new catalysts according to the invention are colorless compounds, the preferred types being liquid. They are soluble in organic solvents and are soluble or dispersible in water. The quantity of these compounds used as catalysts is generally about 0.01 to 5% by weight, based on the compound containing the active hydrogen atoms. Although it is possible to use more than the quantity mentioned above, this does not afford any advantages.

The compounds containing active hydrogen atoms or isocyanate-reactive groups which are used as component b) in the process according to the invention are known and have previously been used for the production of polyurethanes. Note, for example, Kunststoff-Handbuch, Vol. VII, Polyurethane, Hansen-Verlag, Munchen, 1983, pages 42–62 or in Houben-Weyl, Makromolekulare Stoffe, Vol. E20, pages 1595–1604.

The compounds containing NCO groups used in accordance with the invention as component a) are also known and have previously been used for the production of polyurethanes. Note, for example, Kunststoff-Handbuch, Vol. VII, Polyurethane, Hansen-Verlag, Munchen 1983, or in Houben-Weyl, Makromolekulare Stoffe, Vol. E20.

In the process according to the invention, the substituted triamino(imino)phosphoranes are used in the same way as known catalysts. For example, the catalyst may be used as such in its liquid form or by dissolution in a polyol or suitable solvent. It may be used at any temperature—or other conditions—either individually or in combination with known catalysts for the production of polyurethanes, including for example organic or inorganic tin compounds or other organometallic compounds; tertiary amines; alkanolamines; cyclic amines; polyamines; alkali metal compounds; and other cocatalysts.

The process according to the invention is suitable for conventional production methods, including the one-shot process or prepolymer process for the production of polyurethane foams, polyurethane elastomers, polyurethane coatings, etc., and for cross-linking reactions which are often desirable after the initial polyaddition reaction.

All other conditions are the same as in conventional urethane polyaddition processes. In each of these cases, it is possible to use other known such as chain-extending agents, blowing agents, foam stabilizers, emulsifiers, dyes, pigments and fillers.

The above-mentioned catalysts according to the invention accelerate the polyaddition to a considerable extent, so that the quantity of catalyst required is very small. Since the compounds according to the invention have only a weak odor and because they are not volatile liquids or solids, the polyurethane products obtained are free from unwanted odors.

The following examples are intended to illustrate the invention without limiting it in any way. In all of the examples, parts and ratios are by weight.

EXAMPLES

Example 1

This example demonstrates the catalytic activity of the triamino(imino)phosphoranes according to the invention in a PUR cold-cure flexible molded foam system using N,N',N''-hexamethyl triamino(methylimino)-phosphorane (prepared by the method described in the specification) which has the following physical characteristics:

Bp. (0.3 mm): 60 to 62° C.

| CHNP analysis: | calculated | found |
|---|---|---|
| C | 43.7 | 44.1 |
| H | 10.9 | 11.0 |
| N | 29.1 | 29.0 |
| P | 16.1 | 16.0 |

Component A:

37.10 parts of a mixture of 2,4-tolylene diisocyanate and 2,6-tolylene diisocyanate in a ratio of 80:20 and 4,4'-diisocyanatodiphenyl methane having polymeric components and an NCO content of 44.5±0.5% by weight; a commercial product of Bayer AG.

Component B: 100.00 parts of a polyether polyol, OH value 28 ±2 mg KOH/g, prepared by reaction of trimethylol propane (TMP) with propylene oxide (PO) and subsequent reaction with ethylene oxide (EO), PO/EO ratio 82:18

3.00 parts water 0.05 parts of a 70% solution of bis-(2-dimethylaminoethyl)-ether in dipropylene glycol (DPG)

0.25 parts of a 33% solution of diazabicyclo-[2.2.2]-octane (DABCO) in DPG 0.20 parts foam stabilizer B 4617, a product of Goldschmidt AG x parts of the triamino(imino)-phosphorane described above.

Component A was combined with component B and the two components were thoroughly mixed for 10 seconds with a high-speed stirrer. The reaction mixture was then foamed at room temperature in an open mold.

The results obtained with various additions of the triamino(imino)phosphorane are shown in Table I below.

TABLE I

| x (parts) | 0 | 0.2 | 0.4 | 0.6 |
|---|---|---|---|---|
| Cream time (secs) | 9 | 7 | 5 | 4 |
| Gel time (secs) | 135 | 60 | 48 | 40 |
| Rise time (secs) | 180 | 130 | 100 | 90 |

The strong catalytic activity of the catalyst is clearly apparent.

Example 2

This example demonstrates the activity of the new catalysts by comparison with diazabicyclo-[2,2,2]-octane (DABCO) in a PUR cold-cure flexible molded foam.

Processing is carried out as in Example 1. Foam 1 containing the catalyst of Example 1 according to the invention:

Component A:
33.40 parts of the isocyanate of Example 1
Component B:
100.00 parts of the polyol of Example 1
3.20 parts water
0.12 parts of a 70% solution of bis-(2-dimethylaminoethyl)-ether in dipropylene glycol (DPG)
0.10 parts of the foam stabilizer of Example 1
0.30 parts of the catalyst of Example 1
Foam 2 containing DABCO for comparison:

The formulation was the same as used for foam 1, except that the catalyst according to the invention was replaced by 0.5 part of a 33% solution of DABCO in dipropylene glycol.

Both foam 1 and comparison foam 2 had open cells and were highly elastic. The cells were of normal size. The cream, gel and rise times are shown in Table 2.

TABLE 2

|  | Foam 1 | Comparison Foam 2 |
|---|---|---|
| Cream time | 5 secs | 5 secs |
| Gel time | 50 secs | 50 secs |
| Rise time | 85 secs | 85 secs |

This example shows that the catalysts according to the invention are at least as active as DABCO.

Example 3

This example demonstrates the catalytic effect of the compounds according to the invention in an aliphatic flexible foam:

Component A:

41 parts isophorone diisocyanate pre-reacted with a polyether polyol (OH value 670 g KOH/g), prepared by the propoxylation of glycerol to form a semiprepolymer having an NCO content of 29% by weight.

Component B:

80.00 parts of a polyether polyol (OH value 268 g KOH/g), prepared by the reaction of trimethylol propane with propylene oxide (PO) and subsequent reaction with ethylene oxide (EO), PO/EO ratio 78:22

7.00 parts ethylene glycol
0.50 parts dibutyl tin dilaurate
5.00 parts trichlorofluoromethane
0.50 parts of the catalyst of Example 1.

Processing was carried out as in Example 1.

The cream time of the system was 10 seconds and the rise time 2 minutes.

Example 4

This example demonstrates the catalytic activity of another representative of the triamino(imino)phosphoranes, i.e., 2-t-butylimino-2-diethylamino-1,3-dimethyl-perhydro-1,3,2-diazaphosphorine, in a flexible foam system. This catalyst was prepared by the method described in the specification.

GC purity: >98%
Bp (0.03 Torr): 72° C.
Component A:
18 parts of a mixture of 2,4-tolylene diisocyanate and 2,6-tolylene diisocyanate in a ratio of 80:20
Component B:
50.00 parts of a polyether polyol (OH value 35 mg KOH/g) prepared by the reaction of trimethylol propane with propylene oxide (PO) and subsequent reaction with ethylene oxide (EO), PO/EO ratio 86.55:13.45
1.50 parts water
0.50 parts of a polyether polysiloxane as stabilizer, Stabilisator OS 50, a product of Bayer AG
0.30 parts of the triamino(imino)phosphorane described above.

Component B was stored at room temperature and, after various periods of storage, was processed as in Example 1 with the addition of 0.05 parts tin(II) octoate.

|  | Cream time | Rise time |
| --- | --- | --- |
| Comparison (0 days) | 6 secs | 105 secs |
| Storage time: | | |
| 1 day | 6 secs | 101 secs |
| 8 days | 6 secs | 103 secs |
| 20 days | 7 secs | 104 secs |

It can be seen that storage of the water-containing component B for three weeks had no effect on the catalytic activity of the catalyst according to the invention.

Example 5

This example demonstrates the hydrolysis stability of the catalysts according to the invention by comparison with 1,8-diazabicyclo-[5,4,0]-undec-7-ene (DBU).

The following aqueous solutions were prepared:

Solution 1: 0.3 parts catalyst of example 1 in 1.5 parts water

Solution 2: 0.3 parts catalyst of example 4 in 1.5 parts water

Solution 3: 0.3 parts DBU in 1.5 parts water

Component A:
18 parts of the isocyanate of Example 4

Component B;

| 50.00 | parts of the polyol described in Example 5 |
| --- | --- |
| 0.50 | parts of the stabilizer of Example 5 |
| 0.05 | parts tin(II) octoate |
| 1.80 | parts of solution 1, 2 or 3. |

After the aqueous solutions had been stored for various periods, the following results were obtained:

|  | Cream time | Rise time |
| --- | --- | --- |
| Comparison without storage | | |
| Solution 1 | 5 secs | 70 secs |
| Solution 2 | 6 secs | 105 secs |
| Solution 3 | 10 secs | 90 secs |
| After 4 days | | |
| Solution 1 | 6 secs | 105 secs |
| Solution 2 | 6 secs | 108 secs |
| Solution 3 | 12 secs | 195 secs |
| After 18 days | | |
| Solution 1 | 6 secs | 105 secs |
| Solution 2 | 6 secs | 105 secs |
| Solution 3 | 23 secs | 210 secs |

In contrast to the catalysts according to the invention, DBU underwent a marked reduction in its catalytic activity in aqueous solution.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of optionally cellular polyurethane by the isocyanate polyaddition process which comprises reacting a) a polyisocyanate with b) a compound containing at least two isocyanate-reactive groups and c) a catalyst comprising one or more triamino(imino)-phosphoranes corresponding to the following formulas

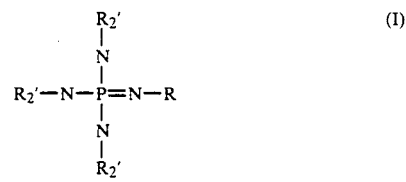

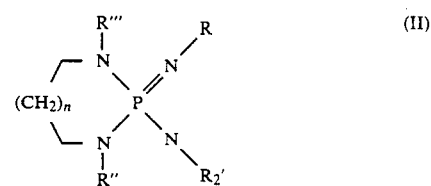

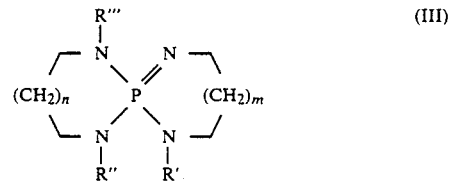

wherein

R represents hydrogen, a linear or branched alkyl group containing 1 to 8 carbon atoms, a cycloalkyl or alkylcycloalkyl group containing 5 to 9 carbon atoms, an aryl group or an alkylaryl group, R' represents a linear or branched alkyl group containing 1 to 8 carbon atoms, a cycloalkyl or an alkylcycloalkyl group containing 5 to 9 carbon atoms or a cycloalkylene group containing 4 to 6 carbon atoms, R" represents hydrogen, a linear or branched alkyl group containing 1 to 8 carbon atoms, a cycloalkyl or an alkylcycloalkyl group containing 5 to 9 carbon atoms, an aryl group or an alkylaryl group, R'" represents a linear or branched alkyl group containing 1 to 8 carbon atoms, a cycloalkyl or an alkylcycloalkyl group containing 5 to 9 carbon atoms, an aryl group or an alkylaryl group and n and m may be the same or different and represent 0, 1, or 2.

* * * * *